(12) United States Patent
Farris et al.

(10) Patent No.: US 7,001,387 B2
(45) Date of Patent: *Feb. 21, 2006

(54) ANTERIOR CERVICAL PLATING SYSTEM (75) Inventors: Robert A. Farris, Memphis, TN (US);
Jeffrey Wade Poyner, Atoka, TN (US);
Volker K. H. Sonntag, Phoenix, AZ
(US); Regis W. Haid, Jr., Atlanta, GA
(US); Stephen M. Papadopoulos, Ann
Arbor, MI (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/713,949

(22) Filed: Nov. 13, 2003

(65) Prior Publication Data

US 2004/0097934 A1   May 20, 2004

Related U.S. Application Data

(63) Continuation of application No. 09/723,317, filed on Nov. 27, 2000, now Pat. No. 6,669,700, which is a continuation of application No. 09/399,525, filed on Sep. 20, 1999, now Pat. No. 6,152,927, which is a continuation of application No. 08/856,902, filed on May 15, 1997, now abandoned.

(51) Int. Cl.
*A61B 17/80* (2006.01)

(52) U.S. Cl. .................. 606/69; 606/61; 606/70; 606/73

(58) Field of Classification Search .......... 606/60, 606/61, 69, 70, 71, 72, 73
See application file for complete search history.

(56) References Cited

U.S. PATENT DOCUMENTS 3,659,595 A    5/1972    Haboush (Continued)

FOREIGN PATENT DOCUMENTS

EP    0 251 583    6/1987

(Continued)

*Primary Examiner*—David O. Reip
(74) *Attorney, Agent, or Firm*—Krieg DeVault, LLP (57) ABSTRACT

In one embodiment of the invention, an anterior fixation system includes a plate defining a plurality of screw holes, a number of screws and a number of locking assemblies for fixing the screws to the plate. The system includes two bone screws a fixed angle screw and a variable angle screw, that are configured to extend through the same screw openings in the fixation plate. The surgeon can select either the fixed or variable angled screws to be implanted with a single plate and can place either type of screw into any of the screw holes along the plate. The fixation plate according to the invention can include several screw holes in various patterns that provide the surgeon with great flexibility in the placement of bone screws depending upon the spinal anatomy and pathology. The invention further contemplates a locking assembly to lock one or more bone screws within a respective screw hole. In one embodiment, the locking assembly includes a washer that is held to the plate by a staked locking screw. The washer includes an outer surface that overlaps one or more screw holes. The washer is initially loosely held to the plate by the locking screw so that various tools and bone screws can be passed through the screw holes. In one embodiment of the washer, the washer includes cut-outs corresponding to the screw holes, along with a notch and key configuration for setting the locking washer in its locked configuration.

16 Claims, 7 Drawing Sheets

U.S. PATENT DOCUMENTS

| | | | |
|---|---|---|---|
| 3,741,205 A | 6/1973 | Markolf et al. | |
| 4,334,599 A | 6/1982 | Ritsema et al. | |
| 4,388,921 A | 6/1983 | Sutter et al. | |
| 4,488,543 A | 12/1984 | Tornier | |
| 4,493,317 A | 1/1985 | Klaue | |
| 4,503,848 A | 3/1985 | Caspar et al. | |
| 4,776,330 A | 10/1988 | Chapman et al. | |
| 4,794,918 A | 1/1989 | Wolter | |
| 5,041,113 A | 8/1991 | Biedermann et al. | |
| 5,041,114 A | 8/1991 | Chapman et al. | |
| 5,057,111 A | 10/1991 | Park | 606/69 |
| 5,108,395 A | 4/1992 | Laurain | 606/61 |
| 5,113,685 A | 5/1992 | Asher et al. | |
| 5,127,912 A | 7/1992 | Ray et al. | 606/61 |
| 5,147,361 A | 9/1992 | Ojima et al. | 606/61 |
| 5,190,544 A | 3/1993 | Chapman et al. | |
| 5,261,910 A | 11/1993 | Warden et al. | |
| 5,304,179 A | 4/1994 | Wagner | |
| 5,324,290 A | 6/1994 | Zdeblick et al. | 606/61 |
| 5,326,206 A | 7/1994 | Moore | |
| 5,364,399 A | 11/1994 | Lowery et al. | 606/69 |
| 5,380,323 A | 1/1995 | Howland | |
| 5,382,248 A | 1/1995 | Jacobson et al. | |
| 5,397,363 A | 3/1995 | Gelbard | |
| 5,423,826 A | 6/1995 | Coates et al. | 606/96 |
| 5,534,032 A | 7/1996 | Hodorek | |
| 5,549,612 A | 8/1996 | Yapp et al. | 606/69 |
| 5,569,247 A | 10/1996 | Morrison | |
| 5,578,034 A | 11/1996 | Estes | 606/61 |
| 5,601,553 A | 2/1997 | Trebing et al. | 606/61 |
| 5,616,144 A | 4/1997 | Yapp et al. | |
| 5,620,443 A | 4/1997 | Gertzbein et al. | 606/61 |
| 5,647,872 A | 7/1997 | Gilbert et al. | |
| 5,653,708 A | 8/1997 | Howland | |
| 5,676,666 A | 10/1997 | Oxland et al. | 606/61 |
| 5,681,311 A | 10/1997 | Foley et al. | 606/69 |
| 5,709,686 A | 1/1998 | Talos | |
| 5,735,850 A | 4/1998 | Baumgartner et al. | |
| 5,735,853 A | 4/1998 | Olerud | |
| 5,797,912 A | 8/1998 | Runciman et al. | |
| 5,800,433 A | 9/1998 | Benzel et al. | |
| 5,807,396 A | 9/1998 | Raveh | 606/69 |
| 5,843,082 A | 12/1998 | Yuan et al. | |
| 5,904,683 A | 5/1999 | Pohndorf et al. | |
| 5,951,558 A | 9/1999 | Fiz | 606/70 |
| 5,954,722 A | 9/1999 | Bono | |
| 5,976,141 A | 11/1999 | Haag et al. | |
| 5,984,924 A | 11/1999 | Asher et al. | |
| 6,022,350 A | 2/2000 | Ganem | |
| 6,030,389 A | 2/2000 | Wagner | |
| 6,132,434 A | 10/2000 | Sherman et al. | |
| 6,139,550 A | 10/2000 | Michelson | 606/69 |
| 6,152,927 A | 11/2000 | Farris et al. | |
| 6,193,721 B1 | 2/2001 | Michelson | 606/70 |
| 6,224,602 B1 | 5/2001 | Hayes | 606/69 |
| 6,235,034 B1 | 5/2001 | Bray | |
| 6,261,291 B1 | 7/2001 | Talaber et al. | |
| 6,290,703 B1 | 9/2001 | Ganem | |
| 6,322,562 B1 | 11/2001 | Wolter | |
| 6,413,259 B1 | 7/2002 | Lyons et al. | |

FOREIGN PATENT DOCUMENTS

| | | |
|---|---|---|
| EP | 0 455 255 A1 | 11/1991 |
| EP | 0 471 418 B1 | 2/1992 |
| EP | 0 599 640 A1 | 1/1994 |
| FR | 2 519 857 | 7/1983 |
| FR | 2 556 583 | 7/1985 |
| FR | 2 740 321 | 4/1997 |
| WO | WO 91/03994 | 4/1991 |
| WO | WO 94/17744 | 8/1994 |
| WO | WO 96/29948 A1 | 10/1996 |
| WO | WO 98/34553 | 8/1998 |
| WO | WO 98/34556 | 8/1998 |

ANTERIOR CERVICAL PLATING SYSTEM

CROSS REFERENCE TO RELATED APPLICATIONS

This application is a continuation of U.S. patent application Ser. No. 09/723,317 filed on Nov. 27, 2000, now issued as U.S. Pat. No. 6,669,700 and which is incorporated herein by reference; which is a continuation of U.S. patent application Ser. No. 09/399,525 filed on Sep. 20, 1999, and now issued as U.S. Pat. No. 6,152,927; which is a continuation of U.S. patent application Ser. No. 08/856,902 filed on May 15, 1997, now abandoned.

BACKGROUND OF THE INVENTION

The present invention concerns spinal instrumentation systems, most particularly for use in fixation of the cervical spine. More particularly, the invention pertains to a plating system for use in the treatment of various spinal pathologies.

As with any bony structure, the spine is subject to various pathologies that compromise its load bearing and support capabilities. The spine is subject to degenerative diseases, the effects of tumors and, of course, fractures and dislocations attributable to physical trauma. Throughout the last century, spinal surgeons have tackled the thorny problems associated with addressing and correcting these pathologies using a wide variety of instrumentation and a broad range of surgical techniques. For many years, the use of elongated rigid plates has been helpful in the stabilization and fixation of the lower spine, most particularly the thoracic and lumbar spine. These same plating techniques have found a tougher road towards acceptance by surgeons specializing in treatment of the cervical spine.

The cervical spine can be approached either anteriorly or posteriorly, depending upon the spinal disorder or pathology to be treated. Many of the well known surgical exposure and fusion techniques of the cervical spine are described in a publication entitled *Spinal Instrumentation,* edited by Drs. Howard An and Jerome Cotler. This text also describes instrumentation that has been developed in recent years for application to the cervical spine, most frequently from an anterior approach.

The anterior approach to achieving fusion of the cervical spine has become the most popular approach. During the early years of cervical spine fusion, the fusions occurred without internal instrumentation, relying instead upon external corrective measures such as prolonged recumbent traction, the use of halo devices or minerva casts, or other external stabilization. However, with the advent of the elongated plate customized for use in the cervical spine, plating systems have become predominant for this type of spinal surgery.

It has been found that many plate designs allow for a uni-corticaly or bi-corticaly intrinsically stable implant. It has also been found that fixation plates can be useful in stabilizing the upper or lower cervical spine in traumatic, degenerative, tumorous or infectious processes. Moreover, these plates provide the additional benefit of allowing simultaneous neural decompression with immediate stability.

During the many years of development of cervical plating systems, particularly for the anterior approach, various needs for such a system have been recognized. For instance, the plate must provide strong mechanical fixation that can control movement of each vertebral motion segment in six degrees of freedom. The plate must also be able to withstand axial loading in continuity with each of the three columns of the spine. The plating system must be able to maintain stress levels below the endurance limits of the material, while at the same time exceeding the strength of the anatomic structures or vertebrae to which the plating system is engaged.

Another recognized requirements for a plating system is that the thickness of the plate must be small to lower its prominence, particularly in the smaller spaces of the cervical spine. The screws used to connect the plate to the vertebrae must not loosen over time or back out from the plate. Preferably the plate should be designed to contact the vertebrae for greater stability.

On the other hand, while the plate must satisfy certain mechanical requirements, it must also satisfy certain anatomic and surgical considerations. For example, the cervical plating system must minimize the intrusion into the patient and reduce the trauma to the surrounding soft tissue. In the *Spinal Instrumentation* text, as well as in other documentation in this field, it is stressed that complications associated with any spinal procedure, and most particularly within the tight confines of cervical procedures, the complications can be very devastating, such as injury to the brain stem, spinal cord or vertebral arteries. It has also been found that optimum plating systems permit the placement of more than one screw in each of the instrumented vertebrae.

Many spinal plating systems have been developed in the last couple of decades that address some of the needs and requirements for cervical fixation systems. However, even with the more refined plating system designs, there still remains a need for a system that has universal applicability to all pathologies that can be faced by a spinal surgeon in treating the spine. For example, it has been demonstrated that different degrees of fixation of a bone screw relative to the plate are more advantageous for treating certain pathologies as opposed to other pathologies.

More specifically, it is known that bone screws can be supported in a spinal plate in either a rigid or a semi-rigid fashion. In a rigid fashion, the bone screws are not permitted any micro-motion or angular movement relative to the plate. In the case of a semi-rigid fixation, the bone screw can move somewhat relative to the plate during the healing process of the spine. It has been suggested that semi-rigid fixation is preferable for the treatment of degenerative diseases of the spine. In cases where a graft is implanted to replace the diseased vertebral body, the presence of a screw capable of some rotatation ensures continual loading of the graft. This continual loading avoids stress shielding of the graft, which in turn increases the rate of fusion and incorporation of the graft into the spine.

Similarly, rigid screw fixation is believed to be preferable in the treatment of tumors or trauma to the spine, particularly in the cervical region. It is believed that tumor and trauma conditions are better treated in this way because the rigid placement of the bone screws preserves the neuro-vascular space and provides for immediate stabilization. It can certainly be appreciated in the case of a burst fracture or large tumorous destruction of a vertebra that immediate stabilization and preservation of the disc space and neuro space is essential. On the other hand, the semi-rigid fixation is preferable for degenerative diseases because this type of fixation allows for a dynamic construct. In degenerative conditions, a bone graft is universally utilized to maintain either the disc space and/or the vertebral body itself. In most cases, the graft will settle or be at least partially resorbed into the adjacent bone. A dynamic construct, such as that provided by semi-rigid bone screw fixation, will compensate for this phenomenon.

At present, no plating system is known that allows for the placement of bone screws in either a semi-rigid or a rigid construct with a single plate. While some plates will provide for either one of these screw fixations, no plating system allows the surgeon to use a single plate and to select which of the two types of fixation is desired for the particular spinal pathology and anatomy.

SUMMARY OF THE INVENTION

In order to address the neds left unfulfilled by prior systems, the present invention contemplates a novel system for anterior fixation of the spine utilizing an elongated fixation plate. In one aspect of the invention, the fixation plate is provided with a plurality of holes through which bone screws extend for engagement into a number of vertebrae. In the preferred embodiment, the screw holes include a spherical portion to receive a complementary formed spherical head of the bone screw. The screw holes further include a cylindrical portion integral with the cylindrical portion and opening to the bottom of the plate.

The flexibility of the present invention anterior fixation plating system is accomplished by the provision of a fixed angle and a variable angle screw that can be supported within the same screw hole in the plate. Each of the screws includes a threaded shank for screwing into a vertebra and a spherical head to seat within the spherical recess. Both screws include an intermediate portion between the spherical head and the threaded shank that is configured to reside within the cylindrical portion of the screw hole when the screw is fixed to the plate. The intermediate portion of the fixed angle screw preferably is cylindrical and has an outer diameter sized for a close fit within the cylindrical portion of the screw hole in this manner, the fixed angle screw is prevented from rotating or pivoting within the screw hole.

The variable angle bone screw includes an intermediate portion that is also preferably cylindrical. However, the cylindrical intermediate portion of the variable angle screw has an outer diameter that is significantly smaller than the diameter of the cylindrical portion of the screw hole. This relative difference in diameters between the screw intermediate portion and the screw hole allows the screw to assume a range of angles relative to the bottom surface of the plate, even when the screw is locked in position in the plate.

In a further aspect of the invention, a locking assembly is provided for locking the bone screws in the plate, thereby preventing screw back-out. In one embodiment of the invention, the locking assembly includes a washer that resides within a recess in the plate. The recess overlaps at least one screw hole in the plate so that the washer can be seated above the head of the bone screw to hold the screw in place. The locking assembly further includes a threaded set screw that is engaged within a tapered bore concentrically situated within the washer recess. The locking washer is itself configured with a recess so that the head of the locking screw can reside essentially flush within the locking washer.

In a further embodiment, the locking assembly includes a locking washer having cut-outs formed in its outer surface facing the bone screw head. The cut-outs preferably correspond to the shape of the screw hole so that the washer does not overlap the screw hole in the region of the cut-out. The washer is held to the plate by a set screw to permit rotation of the washer from a first position in which the cut-outs are aligned with the screw holes, to a second position in which the outer surface of the washer overlaps the screw holes to lock the screw heads in position. In a further aspect, the washer includes a number of keys projecting from its underside that are configured to mate within corresponding notches formed in the locking washer recess. The notch and key configuration essentially locks the washer in its position overlapping the screw holes.

The fixation plate assembly of the present invention further contemplates various screw hole arrangements that permit clamping of multiple screws by a single locking assembly. Other hole arrangements are provided that offer several screw fixation options to the surgeon when instrumenting one or more vertebrae. For instance, a four hole arrangement is set forth in which four screw holes a spaced at 90° intervals around a single locking washer and screw assembly. The surgeon can insert either fixed or variable angle screws into any one or more of the four screw holes depending upon the vertebral anatomy.

It is one object of the invention to provide a fixation plate assembly that accommodates either fixed or variable angle screw fixation in a single plate. Another object resides in the provision of a locking assembly that can lock one or more bone screws within the plate.

One benefit achieved by the present invention is that the fixation plate and locking assembly maintain a low profile within the spine. A further benefit is accomplished by the ability to select either a fixed angle or a variable angle screw at any instrumented level and within a single fixation plate.

Other objects and benefits of the invention will become apparent upon consideration of the following written description of the invention, together with the accompanying figures.

DESCRIPTION OF THE FIGURES

FIGS. 3(*a*)–3(*g*) are top elevational views of a fixation plate in accordance with the present invention provided in different sizes and configuration.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

Figures 1, 2:
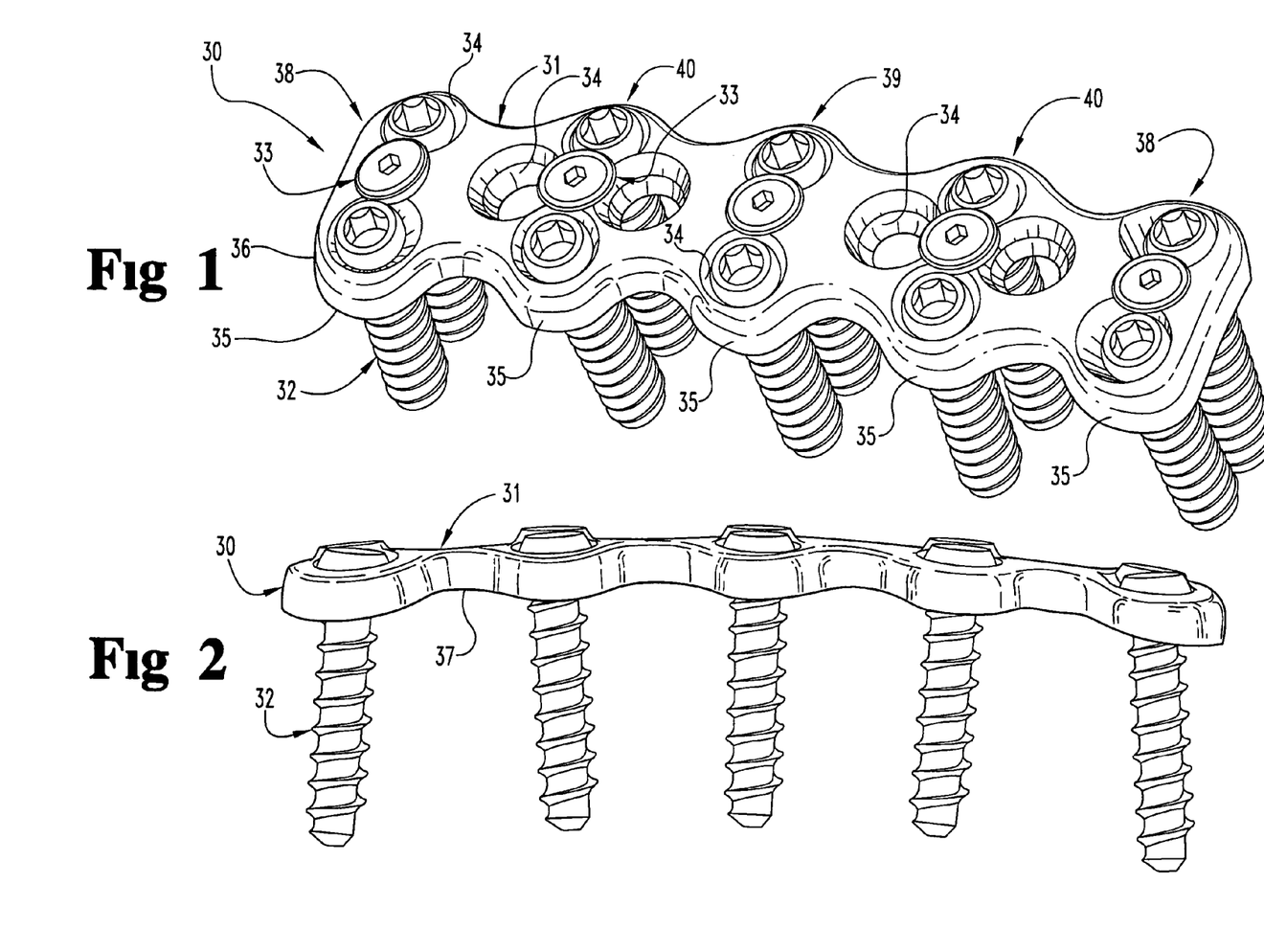
FIG. 1 is a top perspective view of an anterior plating system according to one embodiment of the present invention.
FIG. 2 is a side elevational view of the plating system shown in FIG. 1.

An anterior plating system or fixation assembly 30 is depicted in FIGS. 1 and 2. In accordance with the present invention, the plating system includes an elongated plate 31 and a number of bone screws 32. The bone screws are held to the plate 31 by way of a plurality of locking assemblies 33. The elongated plate 31 is provided with a plurality of screw holes 34 in a variety of arrangements. The plate also can be divided into vertebral level nodes 35 so that the sides of the plate give a serpentine appearance. In particular, the plate 31 includes recesses between each of the nodes 35 to reduce the outer contour and size of the plate. In addition, the reduced width portion between each of the nodes 35 provides an area of reduced material for additional bending of the plate as may be required by the spinal anatomy.

The plate 31 preferably includes a rounded upper edge 36 that would be in contact with the soft tissue surrounding the spine. The rounded edge 36 reduces the amount of trauma that would be experienced by the surrounding soft tissue. The bottom surface 37 of the plate 31 is preferably configured to contact and engage the vertebral bodies at each of the instrumented levels of the spine. In some embodiments, the bottom surface can be textured to enhance its grip on the vertebral body.

Figure 3A:
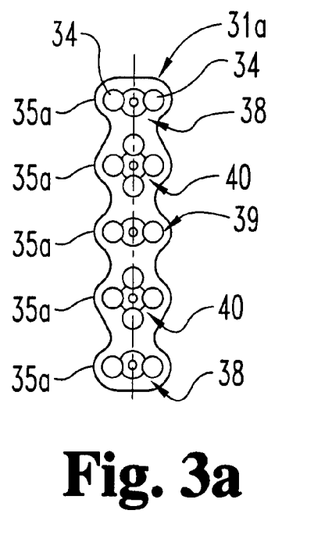
Figure 3B:
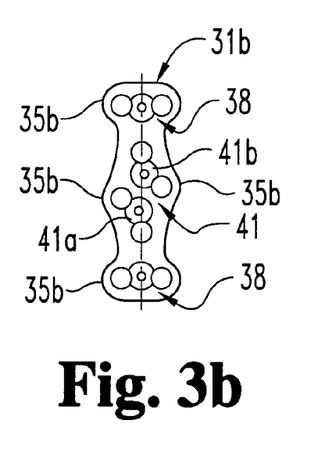

Referring now to FIGS. 3(a)–3(g), several variations of the elongated plate 31 are depicted. It is understood that the anterior plating system according to the present invention can be readily adapted to fix several vertebrae, of course depending upon the length of the plate and the number and arrangement of screw holes 34. The plate depicted in FIGS. 1, 2 and 3(a) includes five vertebral level nodes 35a so that the plate can be engaged to five vertebrae of the spine. For example, the plate 31a of FIG. 3(a) could be used to fix the vertebrae C2–C6. The elongated plates 31b depicted in FIG. 3(b) is sized and configured to span three vertebrae, depending upon the instrumented vertebral levels. In this instance, the plate 31b includes three vertebral level nodes 35b, with two nodes at the opposite ends of the plate and one node with screw holes offset from each other in the middle portion of the plate to accomodate variation in vertebral anatomy.

Figure 3C:
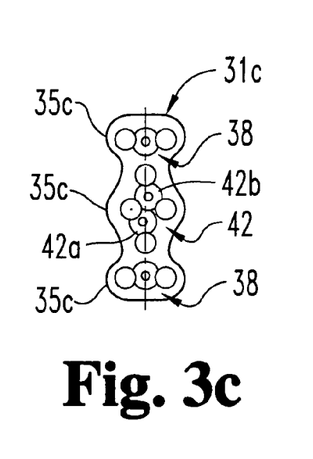

A modification of the plate 31b is depicted in FIG. 3(c). In this case, the plate 31c includes three nodes 35c, with the nodes on the opposite side of the middle portion of the plate being directly aligned at the same vertebral level. The plates of FIGS. 3(d)–3(e), namely plates 31d and 31e, are similar to the plate 31c although their lengths are progressively shorter to accomodate varying vertebral body height. The last two plates 31f and 31g, in FIGS. 3(f)–3(g), respectively, provide for instrumentation of two vertebral levels, each having two nodes 35f and 35g respectively.

In accordance with the present invention, the elongated plates 31a–31g provide a variety of hole patterns at each of the vertebral level nodes 35a–35g. These hole patterns provide, at a minimum, for at least two bone screws to be engaged into each respective vertebra. As discussed above, it has been found that the placement of two or more screws in each vertebral body improves the stability of the construct. It is one object of the present invention not only to provide for multiple screw placement in each vertebral body, but also to provide means for locking the screws to the elongated plate to prevent backout or loosening of the bone screws. Consequently, in a further aspect of the invention, various hole patterns are provided that address these objects. One pattern is an end hole pattern 38, as shown at the ends of plate 31 in FIG. 1 and plate 31a in FIG. 3(a). In this arrangement, two screw holes 34 are laterally disposed at a single node 35a. A single locking assembly is disposed between the two screw holes 34 and is configured to lock bone screws disposed within each respective hole. A similar arrangement is provided by the middle hole pattern 39 in which two screw holes are situated at a single vertebral level. A locking assembly is disposed between the two bone screw holes and is configured to lock bone screws within the respective holes in the same manner as screws are locked in the end hole pattern 38.

Figure 3D:
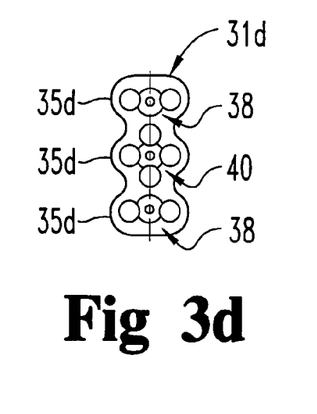
Figure 3E:
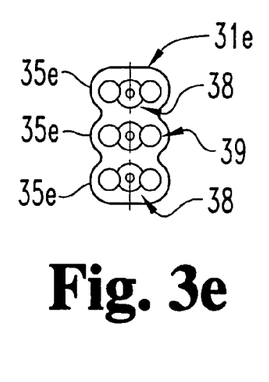

The present invention contemplates a plate carrying four-hole patterns. The four-hole pattern 40 illustrated in FIG. 1 and FIGS. 3(a) and 3(d), provides four bone screw holes 34 in a diamond pattern. A single locking assembly 33 is centrally disposed between all of the bone screw holes so that bone screws within the respective holes are simultaneously locked by the single locking assembly. In the five node plate 31a of FIG. 3(a), two such four-hole patterns 40 are provided. In the three-node plate 31d of FIG. 3(d), only a single four-hole pattern 40 is required. It can be appreciated that the four-hole pattern 40 provides a great degree of flexibility to the surgeon in determining how many bone screws 32 will be engaged into a single vertebra, and in what arrangement. For example, as shown in FIG. 1, two screws are situated in the laterally opposite screw holes at the vertebral level node 35. Alternatively, bone screws could be placed in the longitudinally opposite screw holes oriented along the length of the plate 31a. Less conventional arrangements contemplate bone screws being placed in immediately adjacent screw holes 34, or placing three bone screws in three of the holes of the four-hole pattern 40. Again, the selection of bone screws and their arrangement can be left to the surgeon and will be based upon the type of correction or fixation required and the anatomy of the particular instrumented vertebra.

A further arrangement for screw holes 34 is provided by the four-hole cluster 41 depicted in FIGS. 3(b) and 3(c). In the four-hole cluster 41 in plate 31b, two hole pairs 41a and 41b are provided. Each of the hole pairs includes its own locking assembly to lock the two screws into the screw bores of the respective hole pairs. As shown in FIG. 3(b), the orientation of the particular hole pairs provides one screw hole from each pair generally laterally relative to each other in a single vertebra. The other of the bone screw holes in each respective pair is longitudinally offset from the central screw holes, being disposed closer to the ends of the plate 31b. In this manner, the two central holes of each of the two holes pairs can be engaged in a single vertebra, while the remaining screw holes of the hole pairs 41a and 41b can be disposed in the superior and inferior adjacent vertebrae. Most preferably, however, each of the screw holes in the four-hole cluster 41 is generally oriented over or slightly offset from a single vertebra. The surgeon then has the option to selected any of the screw holes in the two hole pairs 41a or 41b that is optimally aligned over the vertebra.

A similar arrangement is found in the plate 31C which includes a four-hole cluster 42. In this case, it can be seen that the four-hole cluster 42 includes two hole pairs 42a and 42b, in a manner similar to the four-hole cluster 41 of FIG. 3(b); however in this case, the hole pairs are arranged closer to each other, principally because the plate 31C is shorter than the plate 31b. In both of the four-hole clusters 40 and 41, the locking assemblies are provided to lock only a pair of bone screw holes rather than all four holes with a single locking assembly.

Figure 3F:
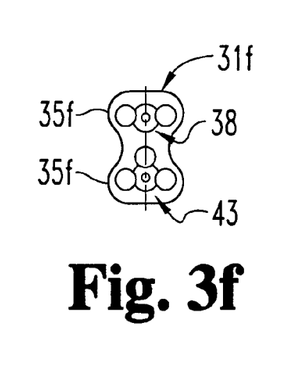
Figure 3G:
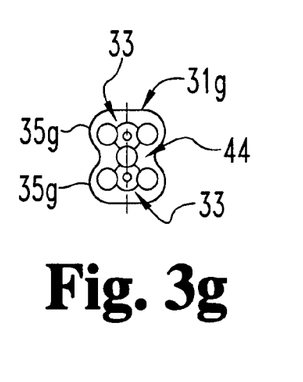

The invention further contemplates a three-hole pattern, such as pattern 43 provided in the plate 31f in FIG. 3(f). In this pattern 43, a single locking assembly is used to fix three bone screws within the respective screw holes. A five-hole pattern 44 is provided on plate 31g, as shown in FIG. 3(g). In this five-hole pattern, a single hole is arranged centrally between four outlying holes. Two locking assemblies 33 are provided to lock a pair of the outlying four screw holes together with the central hole. In this configuration, the central hole is held in place by two locking assemblies, while each of the outlying pair of holes is held in place by a single locking assembly.

Figure 4:
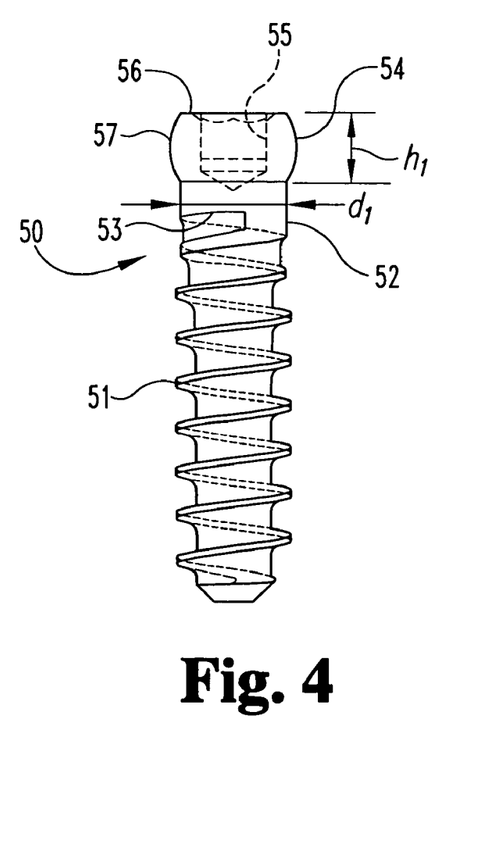
FIG. 4 is a side elevational view of a fixed-angle bone screw according to one aspect of the present invention.
Figure 5:
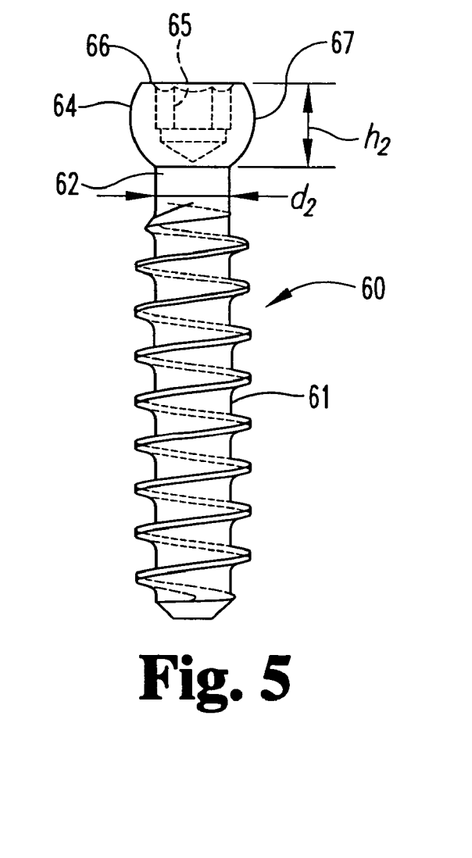
FIG. 5 is a side elevational view of a variable angle bone screw in accordance with another aspect of the present invention.

In one important aspect of the present invention, the bone screw 32 can either constitute a fixed angle screw 50, as shown in FIG. 4, or a variable angle screw 60, as shown in FIG. 5. Turning first to FIG. 4, the fixed angle screw 50 includes a threaded shank 51. The threaded shank is preferably configured to engage the cortical and cancellous bone of a vertebral body. The threaded shank can also include self tapping threads, although the specific illustrated embodiment requires prior drilling and tapping of the vertebral body for insertion of the fixed angle screw 50. The screw 50 includes an intermediate portion 52 that is disposed between the threaded shank 51 and the head 54 of the screw. The threaded shank 51 extends into the intermediate portion 52 by a thread run-out 53, according to standard thread machining practices. As can be seen from FIG. 4, the intermediate portion 52 includes a short segment that does not bear any threads. This short segment has an outer diameter $D_1$ that will assume significance during consideration of the details of the elongated plate 31 discussed herein.

The head 54 of the fixed angle screw 50 includes a tool recess 55 that is configured to receive a driving tool. In one specific embodiment, the tool recess 55 can be a hex recess, or in an alternative embodiment, a TORX* type recess. The head 54 includes a truncated or flattened top surface 56 and a spherical surface 57 between the top surface 56 and the intermediate portion 52. The head 54 includes a height $H_1$ between the top surface 56 and the intermediate portion 52.

In one specific embodiment, the intermediate portion 52, and more specifically the segment between the thread run-out 53 and the head 54, has a height of 1.2 mm and a diameter of 4.05 mm. The height $H_1$ of the head 54 in this specific embodiment has a dimension of 2.6 mm. In this specific embodiment, the dimensions of the head 54 and intermediate portion 52 are calibrated for length of the threaded shank 51 of between 10 mm and 20 mm. In this specific embodiment, the bone screws are preferably configured for engagement in the cervical spine. In another aspect of the specific embodiment, the root diameter of the threaded shank 51 is tapered over the last few convolutions from the initial root diameter to the final root diameter which is 4.05 mm which is about 2.43 mm in the specific embodiment.

Turning to FIG. 5, the details of the variable angle screw 60 can be seen. Like the fixed angle screw 50, the variable angle screw 60 includes a threaded shank 61 and an intermediate portion 62. However, in contrast to the fixed angle screw 50, the intermediate portion 62 has an outer diameter $D_2$ that is approximately equal to the root diameter of the threaded shank 61. In other words, the diameter $D_2$ of the intermediate portion 62 of the variable angle screw 60 is less than the diameter $D_1$ of the intermediate portion 52 of the fixed angle screw 50. Like the fixed angle screw 50, the threads of the shank 61 run out into the intermediate portion 62, leaving the portion 62 with an unthreaded height of about 0.8 mm.

The variable angle screw 60 also includes a head 64 having a tool recess 65 defined from the truncated top surface 66. The head 64 also includes a spherical surface 67 disposed between the top surface 66 and the intermediate portion 62. The head 64 of the variable angle screw 60 has a height $H_2$ between the top surface and the intermediate portion that is greater than the height $H_1$ of the head 54 of the fixed angle screw 50.

In the specific embodiment of the variable angle screw 60, the head 64 has a height $H_2$ of about 3.3 mm. This greater height is attributable to the smaller diameter $D_2$ of the intermediate portion 64 relative to the diameter $D_1$ of the intermediate portion 52 of the fixed angle screw 50. Both the head 54 and the head 64 of the respective screws have a comparable outer diameter, which is 4.88 mm in the specific embodiment. In the case of the variable angle screw, the diameter of the spherical surface 67 continues around a greater arc because the intermediate portion 62 has a smaller diameter. In one specific embodiment, the intermediate portion 62 has a diameter $D_2$ of 2.9 mm, compared to the 4.05 mm diameter $D_1$ for the fixed angle screw 50.

Like the fixed angle screw 50, the variable angle screw 60 can be preferably provided in lengths between 10 mm and 20 mm, for use at different locations in the spine.

Figure 6:
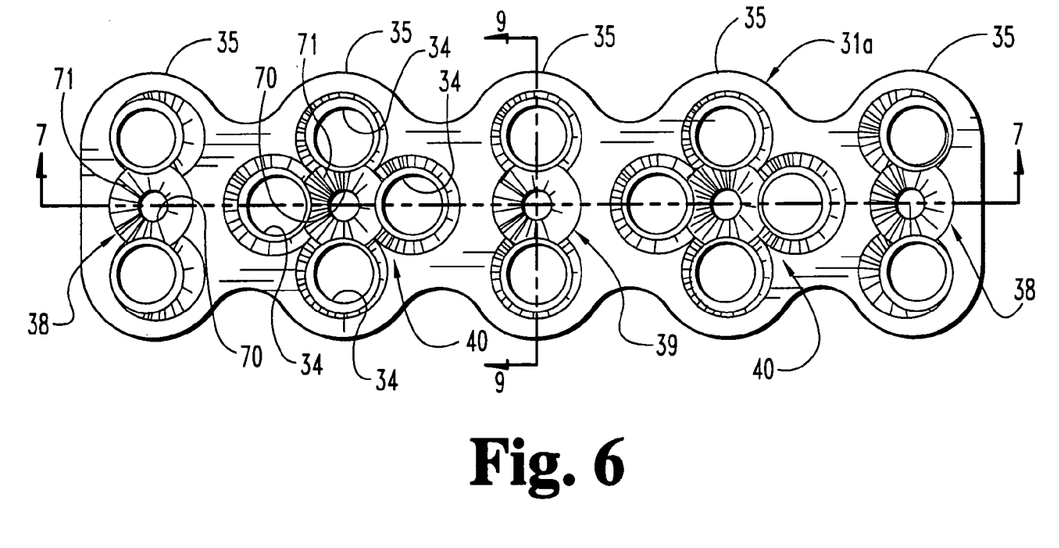
FIG. 6 is a top elevational view of one embodiment of an elongated plate for use with the anterior plating system according to the present invention.
Figure 7:
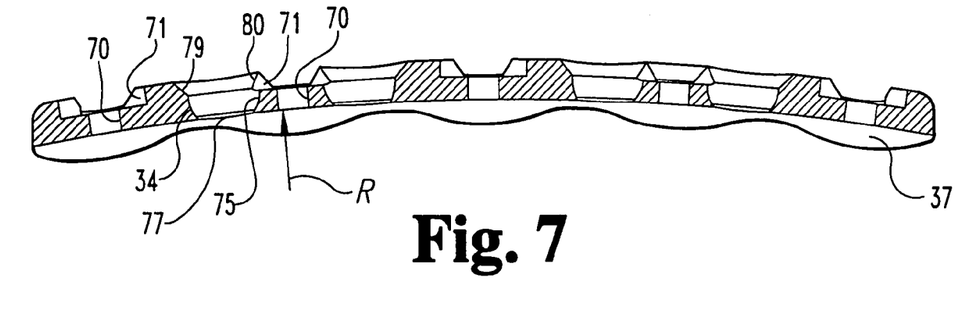
FIG. 7 is a side cross-sectional view of the plate shown in FIG. 6 taken along line 7—7 as viewed in the direction of the arrows.
Figure 8:
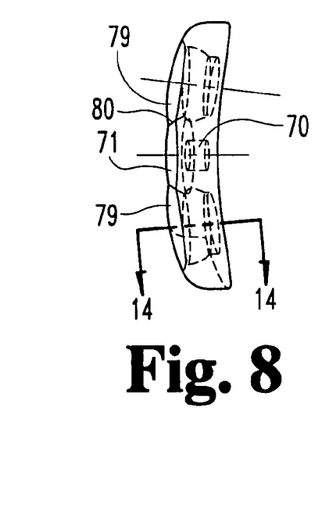
FIG. 8 is an end elevational view of the plate shown in FIG. 6.

The engagement of the bone screws 50 and 60 to the elongated plate 31 require further discussion of the details of the plate itself. These details can be discerned with reference to FIGS. 6–14. In FIG. 6, the longer plate 31a is depicted, although it is understood that the various geometric structural aspects of this plate are repeated among each of the plates 31b–31g. As discussed previously, the plate 31a includes undulating edges, with the peaks of the undulation corresponding to the vertebral level nodes 35. The plate material between the nodes is reduced to minimize the bulk of the plate and to provide a thinner plate width in areas that may require additional bending for implantation. In the specific embodiment, a plurality of screw holes 34 is provided throughout the length of the plate and in various patterns. In the illustrated embodiment of FIG. 6, the holes are oriented in end hole patterns 38 at opposite ends of the plate, middle hole pattern 39 centrally located in the plate, and two four-hole patterns 40 disposed between the end hole patterns 38 and the middle hole pattern 39. In each case, the hole patterns require a locking screw assembly 33. Consequently, the plate 31a, along with all the other plate design contemplated by the present invention, includes tapped bore 70 situated within a concentric locking recess 71. (See FIG. 7). As shown in FIGS. 6 and 7, the locking recess 71 intersects or overlaps adjacent bone screw holes 34. In the case of the end hole pattern 38, the locking recess 71 overlaps the two screw holes, while in the case of the four-hole pattern 40, the locking recess 71 overlaps the four holes 34 arranged in a diamond pattern.

Figure 9:
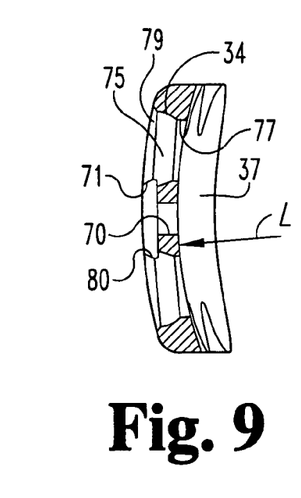
FIG. 9 is an end cross-sectional view of the plate shown in FIG. 6 taken along line 9—9 as viewed in the direction of the arrows.
Figure 10:
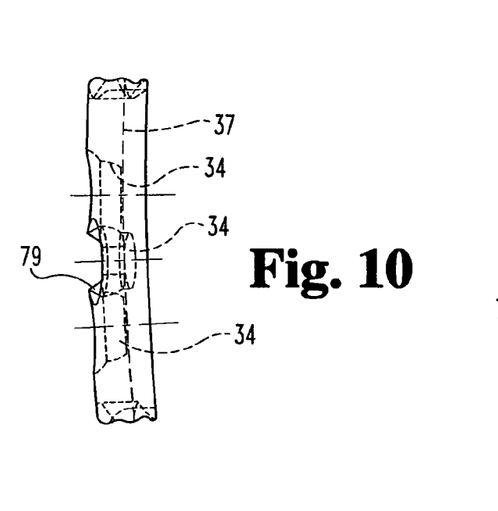
FIG. 10 is a partial side view of a portion of the plate shown in FIG. 6, particularly illustrating the four-hole pattern for the bone screw holes.
Figure 11:
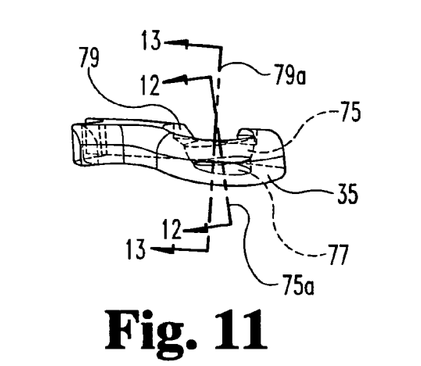
FIG. 11 is a partial side view of an end of the plate in FIG. 6, particularly showing the end hole pattern of bone screw holes.
Figure 12:
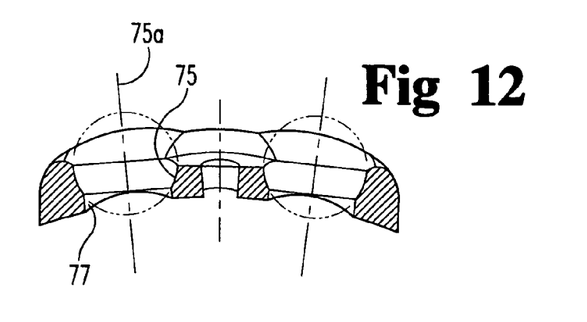
FIG. 12 is a transverse cross-sectional view of the end hole pattern of the plate in FIG. 6, particularly taken along line 12—12 in FIG. 11 as viewed in the direction of the arrows.
Figure 13:
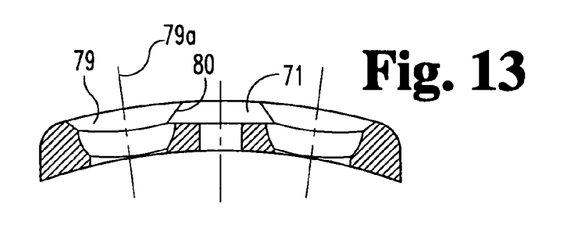
FIG. 13 is an end transverse cross-sectional view of the end of the plate shown in FIG. 6, particularly taken along line 13—13 in FIG. 11 as viewed in the direction of the arrows.

To accommodate the anterior application of this fixation plate assembly 30, the plate is curved medial laterally to approximate the curvate of the vertebral body and longitudinally to approximate the normal lordosis of the cervical spine. Specifically, the bottom surface 37 of the plate can be curved along a large radius R, as shown in FIG. 7, to accommodate the lordotic curvature of the cervical spine. In addition, the bottom surface 37 forms a medial/lateral curvature L, as shown in FIG. 9, to correspond to the curvature of the vertebral body. It is understood that the plate 31a can be bent along its longitudinal length between the vertebral level nodes 35, as required to accommodate the particular spinal anatomy and vertebral pathology.

The screw holes 34 in the plate 31a are defined by a spherical recess 75 (see FIGS. 7 and 9) having a diameter measured about an axis 75a intersecting the elongated plate 31a. (See FIGS. 11 and 12). In a further aspect of the invention, the screw holes 34 include a cylindrical bore 77 communicating between the spherical recess 75 and the bottom surface 37 of the plate 31. The cylindrical bore 77 defines a diameter along the axis 75a. To facilitate insertion of drill guides, drills and the bone screws 32, each screw hole 34 includes a flared recess 79. The flared recess is preferably formed as a tapered counter-sink along an axis 75a (see FIGS. 11 and 12). This flared recess 79 overlaps the locking recess 71 of the locking assembly 33 at a recess overlap 80, shown best in FIGS. 7, 9 and 13.

In one specific embodiment, the spherical recess 75 is defined at a diameter of 5.0 mm, which is slightly larger than the diameter of the heads 54, 64 of the bone screws 50, 60. The cylindrical portion of the screw holes 34 is defined at a diameter of 4.1 mm, in the specific embodiment, which is again slightly larger than the diameter $D_1$ of the intermediate portion 52 of the fixed angle screw 50. It should be understood, of course, that the diameter of the cylindrical bore 77 is significantly larger than the diameter $D_2$ of the intermediate portion 62 of the variable angle screw 60.

Figure 14:
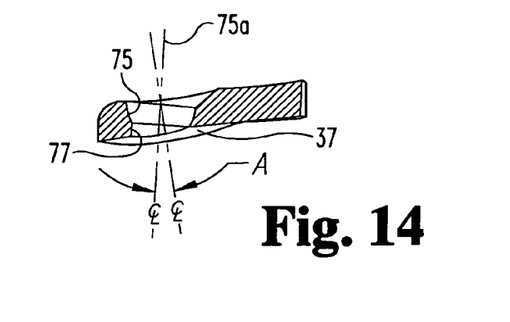
FIG. 14 is a cross-sectional view of one bone screw opening in the end hole pattern of the plate shown in FIG. 6, particularly taken along line 14—14 in FIG. 8 as viewed in the direction of the arrows.

Again in the specific embodiment, the axis 75a of both spherical recess 75, the cylindrical bore 77 and the flared recess 79 is oriented generally normal to the bottom surface 37 of the plate 31a, when viewed in the direction of the longitudinal axis of the plate. In other words, the axis 75a is normal to the plate in the direction of the medial/lateral curvature L of the plate. On the other hand, the orientation of the screw holes 34 can vary between the vertebral level nodes 35, and most particularly when considering the end hole patterns 38. In this specific embodiment, the flared recess 79, is colinear with the axis 75a of the recess 75, for the hole patterns in the interior and end of the elongated plate 31a. For example, as shown in FIG. 6, the flared recess 79 can be approximately concentric with the screw holes 34. On the other hand, the end hole patterns 38, are offset at an angle A, as depicted in FIG. 14. In particular, the axis 75a of the spherical recess, the cylindrical bone 77 and the flared recess 79 is offset at an angle A of about 12 degrees relative to a perpendicular from the bottom surface 37 of the plate 31a. In this manner, the bone screws will be directed outwardly toward the end of the plate upon insertion into the screw holes 34.

Figure 15:
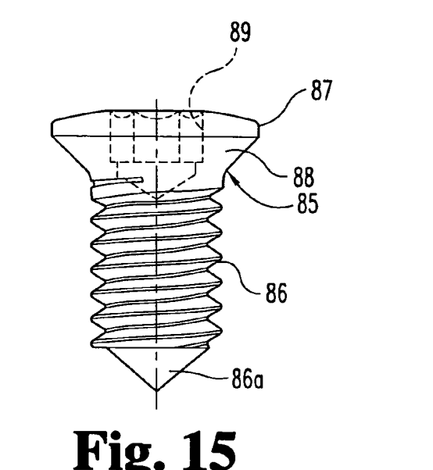
FIG. 15 is an enlarged side elevational view of a locking screw according to one aspect of the present invention.
Figure 16:
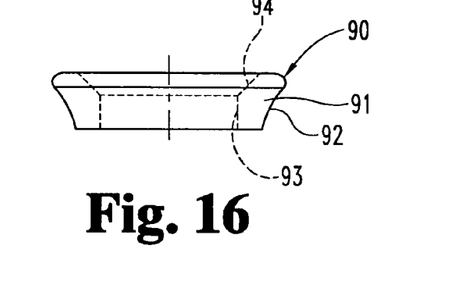
FIG. 16 is an enlarged side elevational view of a locking washer in accordance with a further aspect of the present invention.
Figure 17:
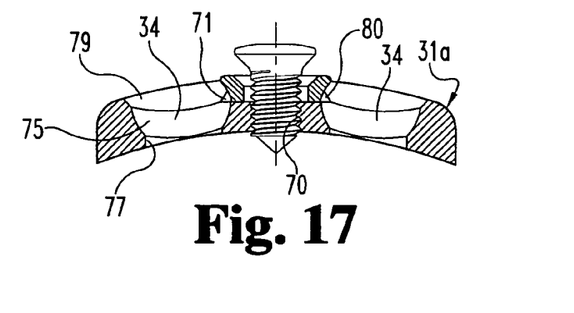
FIG. 17 is a partial cross-sectional view of an end hole pattern of the plate shown in FIG. 6, with the screw and washer of FIGS. 15 and 16, respectively shown in their operative position.

The details of the locking assembly 33 can be gleaned from consideration of FIGS. 15–17. In this specific embodiment, the locking assembly 33 includes a locking screw 85 having machine threads 86. In one specific embodiment, the locking screw 85 terminates in a sharp point 86a to permit penetration of the vertebral body. The head 87 of the locking screw 85 includes a lower conical surface 88 and a tool recess 89 defined therein for receiving a driving tool.

The locking assembly 33 also includes a washer 90 having an outer surface 91. In the specific preferred embodiment, the outer surface 91 is defined by a curved convex surface 92. The washer 90 also includes a screw bore 93 extending therethrough in communication with a tapered bore 94. The tapered bore 94 has a complementary mating configuration relative to the conical surface 88 of the head 87 of locking screw 85. The mating conical features between the locking screw and washer provides a self-centering capability for the washer as the locking screw is tightened onto the plate. The screw, bore 93 is sized to receive the machine threads 86 therethrough for engagement with the tapped bore 70 of the plate 31a, as shown in FIG. 17. As illustrated in FIG. 17, the outer surface 91 of the washer 90 intersects the recess overlap 80 between the flared recess 79 and the respective spherical recess 75 of the adjacent screw holes 34. In a specific embodiment, the locking recess 71 has a diameter of 6 mm to accept the washer 90 having an outer diameter of 5.3 mm. Again in this specific embodiment, the curved convex surface 92 of the washer 90 is curved at a radius of about 2.5 mm so that the lowermost portion of the washer has a smaller diameter of about 4.3 mm.

Figure 18:
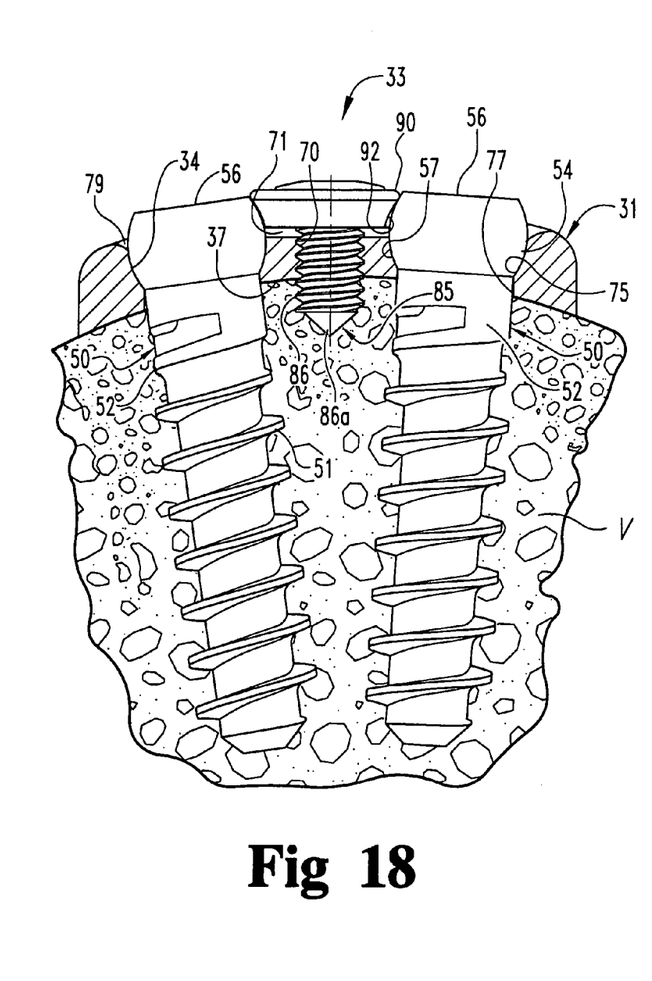
FIG. 18 is a partial cross-sectional view of a plate according to the present invention with the fixed angle bone screws disposed within bone holes in a plate and engaged within a vertebra.
Figure 19:
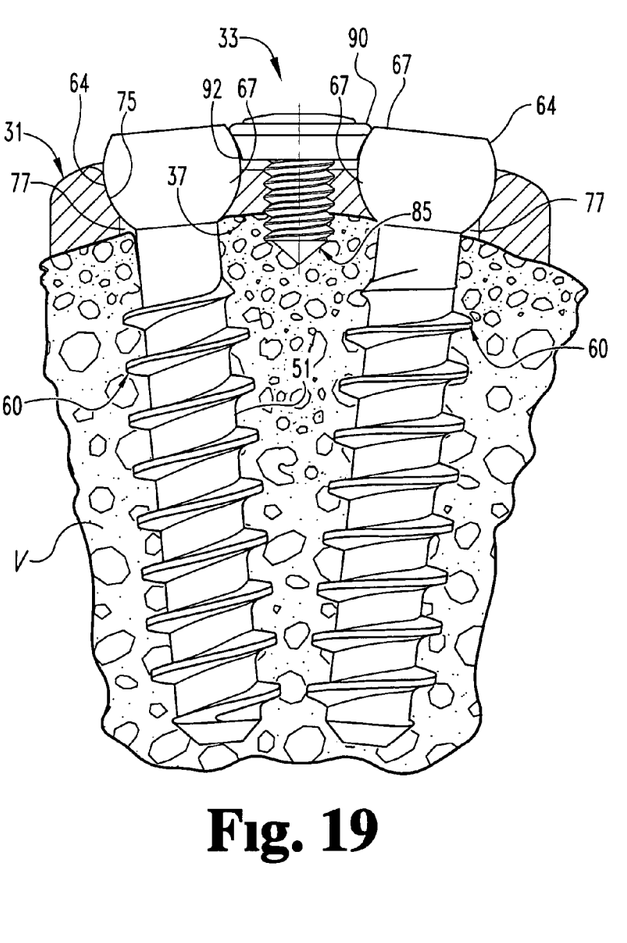
FIG. 19 is an enlarged end cross-sectional view of the plate according to the present invention with variable angle screws disposed in the plate and engaged in a vertebra.

Referring now to FIGS. 18 and 19, the use of the fixation plate assembly 30 is illustrated. In FIG. 18, a pair of fixed angle screws 50 are disposed within respective bores 34 so that the threaded shanks 51 project beyond the lower surface 37 of the plate 31 and into the vertebral body V. The intermediate portion 52 of the fixed angle screw 50 extends through the cylindrical bore 77 of the screw holes 34. The spherical surface 57 of the head 54 of the screw contacts the spherical recess 75 of the screw hole 34 as the fixed angle screw 50 is threaded into the vertebral body V. Once the screw 50 is completely seated within the spherical recess 75, the intermediate portion 52 provides a snug relationship relative to the cylindrical bore 77 so that the fixed angle screw 50 is not able to pivot or translate relative to the plate 31.

In order to ensure secure fixation of the screw 50 within plate 31, the locking assembly 33 is tightened onto the heads 54 of the two bone screws 50. In particular, the locking screw 85 is threaded into the tapped bore 70 to draw the washer 90 into contact with the screw heads. The convex surface 92 seats against the spherical surface 57 of the bone screw heads 54 to firmly seat the screw heads within the plate spherical recess 75. Ine some embodiments, the locking washer 90 can advance sufficiently far into the locking recess 71 to rest substantially flush with the top surfaces 56 of the bone screws 50.

In a further aspect of the invention, the locking assembly 33 is loosely fixed on the plate 31 so that the surgeon need not fiddle with the locking assembly when the plate is engaged to a vertebra. In particular, the locking screw 85 is pre-threaded through the locking washer 90 and into the tapped bore 70 until about three or fewer threads of the locking screw project below the bottom surface 37 of the plate. The locking screw 85 is then staked at the thread furthest from the plate so that the screw cannot be removed or backed out through the tapped bore 70. Of course, the locking screw 85 can be advanced further through the bore 70—when it is necessary to enable the locking assembly 33. As previously mentioned, the sharp point 86a of the locking screw 85 is preferably configured to penetrate the cortical bone. With the locking screw staked to the plate, the sharp point 86a will penetrate the vertebra V when the plate 31 is initially positioned on the bone. In this instance, the locking screw 85 helps locate and temporarily stabilize the plate on the vertebra V as the bone screws 50 are implanted into the bone. This temporary location feature provided by the locking screw 85 can also be used when a drill guide is used to drill and tap the vertebra to receive the bone screws 50.

The locking assembly 33 is configured so that the washer 90 can be moved clear of the screw holes 34 when the locking screw 85 is staked to the plate 31. Thus, even with the locking assembly 33 in its loosened position, the bone screws 50, 60 can still be inserted into the screw holes 34

The use of the variable angle bone screw 60 is depicted in FIG. 19. The locking assembly 33 functions as described above to lock the heads 64 of the variable angle screws 60 within the plate 31. Specifically, the convex surface 92 of the washer 90 contacts and applies pressure to the spherical surfaces 67 of the respective bone screws 60. However, with the variable angle screws 60, the intermediate portion 62 does not fit snugly within the cylindrical bore 77 of the screw holes 34. Thus, even with the head 64 of each screw 60 residing solidly within the spherical recess 75, the bone screw 60 can still be angulated relative to the plate and to the axis of the spherical recess 75 and cylindrical bore 77. It is understood that the degree of angulation is restricted by the difference in diameters between the cylindrical bore 77 and the intermediate portion 62 of the variable angle screw 60. In one preferred embodiment, the relative diameters permit angulation of up to 20° from the axis 75a of the recess 75 and bore 77.

During implantation, the variable angle capability of the screw 60 allows the surgeon to place the bone screw within the vertebra at any angle within the defined angulation limits (20° in one specific embodiment). Thus, the variable angle screw 60 provides greater flexibility than does the fixed angle screw 50 for orienting the bone screw relative to the anatomy of the vertebra. Moreover, this variable angle capability allows a limited degree of micro-motion between the screw and the plate when the fixation assembly 30 is implanted within a patient. In other words, as the spine is loaded and as load is transmitted through the screws and plate, the plate and vertebra may translate relative to each other. The variable angle screw 60 accommodates this relative movement by pivoting within the spherical recess 75. On the other hand, the fixed angle screw 50 prevents this relative movement. The choice between using a fixed or a variable angle screw can be left to the surgeon depending upon the pathology being treated. The fixation plate assembly 30 according to the present invention allows this choice to be made at any point during the surgical procedure.

A further embodiment of the present invention is depicted in FIGS. 20–23. In this embodiment, an alternative locking mechanism is provided. A plate assembly 100 includes an elongated plate 101 receiving bone screws 102. A locking assembly 103 is provided to lock the bone screw within the plate. The plate 101 defines a spherical recess 105 to receive the spherical head 115 of the bone screw. The threaded shank 114 of the bone screw projects through the recess. It is understood that the bone screw 102 and spherical recess 105 can be similar to the like components described above.

Figures 20, 23:
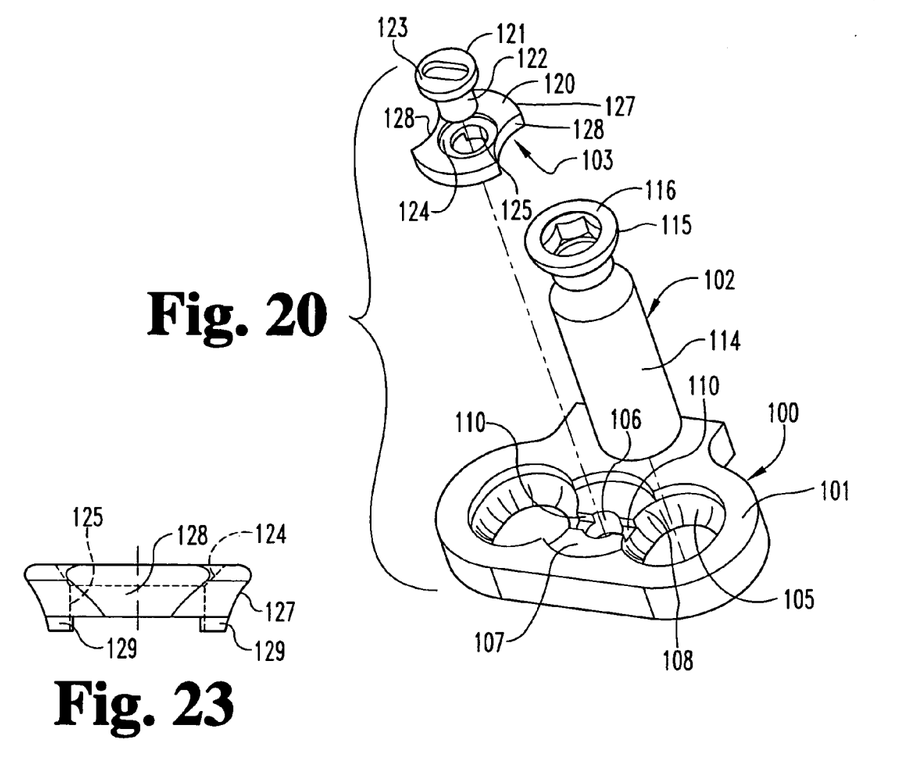
FIG. 20 is an exploded view of an alternative embodiment of a locking screw assembly for use with an anterior plating system according to a further embodiment of the invention.
FIG. 23 is a side elevational view of one embodiment of the locking washer used in the assembly of FIGS. 20–22.

In accordance with this embodiment, the plate further includes a tapped bore and concentric locking recess 107 disposed adjacent the spherical recess 105 for the bone screw. The spherical and locking recess contact at a locking overlap 108. A notch 110 extends transversely across the locking recess 107 in this embodiment.

The locking assembly 103 includes a locking washer 120 and locking screw 121. Like the prior locking screw, the screw 121 includes machine threads 122 and an enlarged head 123. The head sits within a recess 124 in the washer 120, with the machine threads 122 projecting through a bore 125. The machine threads 122 are configured to engage the tapped bore 106 of the plate 101. The locking screw 121 can be staked onto the plate 101 as discussed with respect to the prior embodiment.

Figure 21:
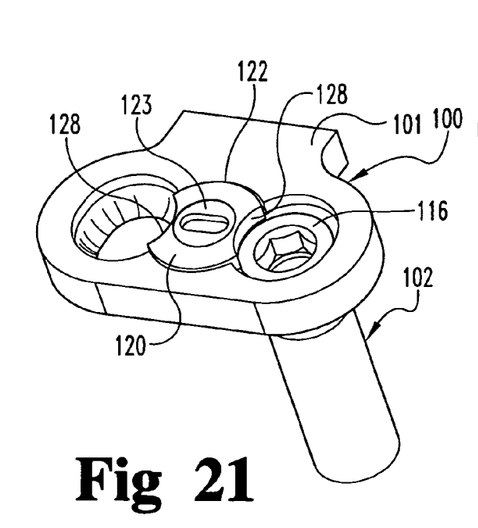
FIG. 21 is a top perspective view of the components shown in FIG. 20 in the assembled condition with the locking washer shown in its first position.

The locking washer 120, while functioning similar to the washer of the prior embodiment offers a different construction than the previous washer. Like the washer 90, the locking washer 120 includes an outer circumferential surface 127 that is preferably convex to mate with a spherical head of the bone screw 102. However, in one modification, the washer 120 includes cut-outs 128 in the circumferential surface 127. The cut-outs 128 are arranged to coincide with the screw recesses 105 when the locking washer is in a first position, as illustrated in FIG. 21. This structure of the washer 120 allows the washer to remain clear of the recess 105 for unimpeded insertion of the bone screw 102.

In certain embodiments, the washer 120 is provided with two such cut-outs at diametrically opposite positions on the washer. Most preferably, the cut-outs 128 are aligned with the relative orientation of screw holes 105 in the plate 101. For example, a washer 120 adapted for a three hole pattern 43, as depicted in FIG. 3(f), would have three cut-outs 128 at 120° intervals. Similarly, a locking washer 120 modified for use with the four hole pattern 40 of FIG. 3(a) would have four cut-outs 128 spaced 90° apart on the circumferential surface 127 of the washer.

Figure 22:
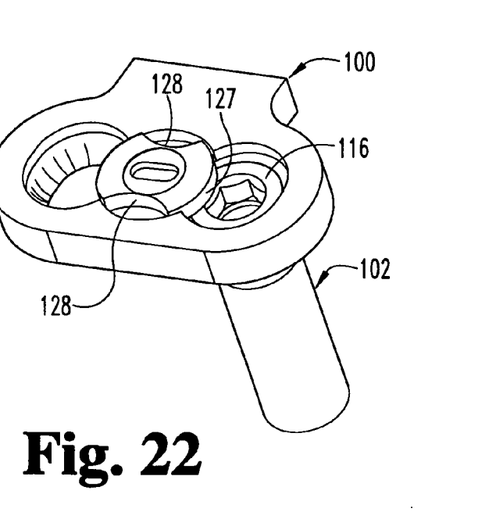
FIG. 22 is a top perspective view of the locking screw as depicted in FIG. 20, with the locking washer in its second position.

Once the bone screws have been implanted through the appropriate screw recesses 105, the locking washer 120 can be rotated into its locking position shown in FIG. 22. In this position, the cut-outs 128 are rotated away from the screw recesses 105 so that the washer, and more particularly the outer circumferential surface 127, overlaps the screw recess 105. In a further modification from the prior washer, the washer 120 includes a number of keys 129 on the underside of the washer. The keys are configured to sit within a corresponding notch 110 in the plate 101 when the locking washer is in the locking position shown in FIG. 22. Once the bone screws have been implanted and the locking washer 120 has been rotated into it locking position, the keys 129 fall into the notches 110 to fix the position of the washer while the locking screw 121 is tightened.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone fixation system comprising:
    an elongated plate having a top surface and a bottom surface and at least two nodes along a length thereof, each of said nodes including first and second holes extending between said top and bottom surfaces, each of said first and second holes including a recessed portion adjacent said top surface having a first diameter and each of said first and second holes defining an opening at said bottom surface having a second diameter less than said first diameter;
    a first bone engaging fastener having a first elongated shank defining bone engaging threads thereon and a first enlarged head at one end thereof, said first shank being configured so that said first bone engaging fastener can be inserted through either of said first and second holes from said top surface of said plate with said first enlarged head at least partially positioned in said recessed portion of said hole, wherein said first bone engaging fastener is further configured so that said first head can be positioned within said recessed portion so that said first elongated shank can assume a plurality of angles relative to said bottom surface of said plate;
    a second bone engaging fastener having a second elongated shank defining bone engaging threads thereon and a second enlarged head at one end thereof, said second shank being configured so that said second bone engaging fastener can be inserted through either of said first and second holes from said top surface of said plate with said second enlarged head at least partially positioned in said recessed portion, wherein said second bone engaging fastener is further configured so that said second head of said second bone engaging fastener cannot be pivoted within said recessed portion and said second shank assumes a fixed orientation relative said bottom surface of said plate; and
    a locking screw assembly for locking said head of said bone engaging fasteners positioned in said recessed portions of said first and second holes of at least one of said nodes, wherein said locking screw assembly includes a washer movable from a first position allowing insertion of said first and second bone engaging fasteners in said first and second holes to a second position overlapping said first and second holes.

2. The system of claim 1, wherein:
    said first bone engaging fastener has a first intermediate portion between said first enlarged head and said first elongated shank, said first intermediate portion having a third diameter that is substantially smaller than said second diameter; and
    said second bone engaging fastener has a second intermediate portion between said second enlarged head and said second elongated shank, said second intermediate portion having a fourth diameter that is approximately equal to said second diameter.

3. The bone fixation system of claim 1, wherein said locking screw assembly includes:
    a fastener bore defined in said plate between said first and second holes of one of said at least two nodes;
    said washer defining a central aperture and a recess communicating with said central aperture, said washer further configured to contact said enlarged heads of said bone engaging fasteners positioned in said recessed portions of said first and second holes; and
    a locking fastener having a head configured to be recessed within said recess of said washer and an elongated shank extending through said central aperture to engage said fastener bore of said plate.

4. The bone fixation system of claim 1, wherein said washer includes an outer circumferential surface with a concave curvature substantially corresponding to a partially spherical surface on each of said enlarged heads of said first and second bone engaging fasteners.

5. A bone fixation system comprising:
    an elongated plate sized to span between at least three vertebrae, said plate defining three sets of two holes, a first set of holes being alignable over a first vertebra, a second set of holes being alignable over a second vertebrae, and a third set of holes being alignable over a third vertebrae, wherein said plate has a top surface and a bottom surface and each of said holes extends between said top and bottom surfaces and includes a recessed portion adjacent said top surface; and
    six bone engaging fasteners, each having an enlarged head and a threaded shank sized to be positioned through said holes, wherein:
        at least one of said six bone engaging fasteners includes a first head that can be pivoted within said recessed portion of said holes so that said first bone engaging fastener can assume a plurality of angles relative to said bottom surface of said plate; and
        at least one of said six bone engaging fasteners includes a second head that cannot be pivoted within said recessed portion of said holes so that said second bone engaging fastener assumes a fixed orientation relative said bottom surface of said plate.

6. The bone fixation system of claim 5, wherein each of said recessed portions is spherical.

7. The bone fixation system of claim 5, further comprising:
    a locking screw assembly for each of said three sets of two holes, each of said locking screw assemblies having a washer configured to overlap an adjacent one of said set of two holes.

8. The bone fixation system of claim 7, wherein said washer has an outer circumferential surface with a concave curvature substantially corresponding to a partially spherical surface of said enlarged heads of said bone engaging fasteners.

9. The bone fixation system of claim 7, wherein each of said locking screw assemblies further includes:
    a fastener bore in said plate adjacent said set of two holes; and
    said washer defining a central aperture, a recess communicating with said aperture, and a bottom surface configured to contact said enlarged heads of bone engaging fasteners in said adjacent set of two holes.

10. The bone fixation system of claim 9, wherein said plate further defines a locking recess in a top surface of said plate in communication with a respective one of said fastener bores and each hole of said adjacent set of two holes includes a flared recess overlapping said locking recess.

11. The bone fixation system of claim 9, wherein said washer includes a first portion overlapping said adjacent set of two holes when said washer is in a first position relative to said two holes and having a second portion that does not overlap said two holes when said washer is in a second position, whereby said bone engaging fasteners can be inserted into said two holes with said washer engaged to said plate when said washer is in said second position.

12. The bone fixation system of claim 11, further comprising a locking fastener having a head configured to be recessed within said recess of said washer and an elongated shank extending through said central aperture and configured to engage said fastener bore of said plate.

13. The bone fixation system of claim 12, wherein said head of said locking fastener defines a lower conical surface for contacting said washer.

14. A system for stabilizing or fixing a first vertebra relative to a second vertebra, comprising:
- a substantially planar rigid structure positionable on at least a portion of both of the first vertebra and the second vertebra;
- a first fastener securable between the substantially planar rigid structure and the first vertebra in a fixed angular position and a first fixed normal position both relative to the substantially planar rigid structure;
- a second fastener securable between the substantially planar rigid structure and the second vertebra in a pivotable angular position and a second fixed normal position both relative to the substantially planar rigid structure; and
- a lock system engageable with the substantially planar rigid structure and the first fastener and the second fastener to hold the first fastener in the first fixed normal position and the second fastener in the second fixed normal position.

15. The system of claim 14, wherein the substantially planar rigid structure comprises a curved bottom surface.

16. The system of claim 14, further comprising a fusion member holdable in a position by the substantially planar rigid structure between the first vertebra and the second vertebra.

* * * * *